United States Patent
Kaneda et al.

(10) Patent No.: US 10,788,441 B2
(45) Date of Patent: Sep. 29, 2020

(54) MEASURING METHOD OF SENSOR USING INTERDIGITATED ARRAY ELECTRODE, MEASURING APPARATUS AND COMPUTER READABLE MEDIUM STORING MEASURING PROGRAM

(71) Applicants: ARKRAY, Inc., Kyoto-shi, Kyoto (JP); Ultizyme International Ltd., Tokyo (JP)

(72) Inventors: Hisashi Kaneda, Kyoto (JP); Yasuhide Kusaka, Kyoto (JP); Koji Sode, Tokyo (JP)

(73) Assignees: ARKRAY, Inc., Kyoto (JP); Ultizyme International Ltd., Tokyo (JP)

( * ) Notice: Subject to any disclaimer, the term of this patent is extended or adjusted under 35 U.S.C. 154(b) by 455 days.

(21) Appl. No.: 15/232,338

(22) Filed: Aug. 9, 2016

(65) Prior Publication Data

US 2017/0045469 A1 Feb. 16, 2017

(30) Foreign Application Priority Data

Aug. 10, 2015 (JP) .................................. 2015-158357
Aug. 1, 2016 (JP) .................................. 2016-151022

(51) Int. Cl.
*G01N 27/327* (2006.01)
*C12Q 1/00* (2006.01)
*G01N 33/49* (2006.01)

(52) U.S. Cl.
CPC ......... *G01N 27/3272* (2013.01); *C12Q 1/006* (2013.01); *G01N 27/3274* (2013.01); *G01N 33/49* (2013.01)

(58) Field of Classification Search
CPC . G01N 27/3272; G01N 27/3274; G01N 33/49
See application file for complete search history.

(56) References Cited

U.S. PATENT DOCUMENTS 6,576,117 B1 * 6/2003 Iketaki ............... G01K 7/00 205/777.5
2002/0125145 A1 * 9/2002 Ohara ............... G01N 27/3274 205/775

(Continued)

FOREIGN PATENT DOCUMENTS

CN 1394280 A 1/2003
CN 101929977 A 12/2010

(Continued)

OTHER PUBLICATIONS

Machine Translation of JP 2004-233294 A; published Aug. 19, 2004; accessed and printed Nov. 23, 2018 (Year: 2018).*

(Continued)

*Primary Examiner* — Edward J. Schmiedel
(74) *Attorney, Agent, or Firm* — Studebaker & Brackett PC

(57) ABSTRACT

A measuring method of measuring a concentration of a target ingredient in a sample by using a sensor including an interdigitated array electrode that includes a first electrode and a second electrode, and a reagent layer on the interdigitated array electrode, the measuring method includes: applying a voltage to between the first electrode and the second electrode; measuring a first current value of an electric current flowing between the first electrode and the second electrode; measuring a second current value of the current flowing between the first electrode and the second electrode; calculating the concentration of the target ingredient in the sample, based on a third current value; calculating a correction value, based on the first current value and the second current value; and a step of correcting the concentration of the target ingredient in the sample, based on the correction value.

7 Claims, 8 Drawing Sheets

(56) References Cited

U.S. PATENT DOCUMENTS

| | | | |
|---|---|---|---|
| 2005/0145490 A1* | 7/2005 | Shinno | C12Q 1/001 204/403.01 |
| 2010/0219084 A1* | 9/2010 | Blythe | C12Q 1/006 205/777.5 |
| 2011/0139634 A1 | 6/2011 | Chou et al. | |
| 2013/0199943 A1 | 8/2013 | Craggs et al. | |
| 2013/0285682 A1 | 10/2013 | Biskupski et al. | |
| 2015/0362501 A1 | 12/2015 | Kurita et al. | |

FOREIGN PATENT DOCUMENTS

| | | | |
|---|---|---|---|
| CN | 103096793 A | | 5/2013 |
| CN | 103901092 A | | 7/2014 |
| EP | 2306190 A1 | | 4/2011 |
| JP | 2004233294 A | * | 8/2004 |
| JP | 2011-075362 A | | 4/2011 |
| WO | 01/57510 A2 | | 8/2001 |
| WO | 2005/114164 A2 | | 12/2005 |
| WO | 2014/112569 A1 | | 7/2014 |

OTHER PUBLICATIONS

The extended European search report issued by the European Patent Office dated Dec. 23, 2016, which corresponds to European Patent Application No. 16183179.7-1554 and is related to U.S. Appl. No. 15/232,338; 11pp.

An Office Action issued by the European Patent Office dated Mar. 14, 2019, which corresponds to European Patent Application No. 16 183 179.7 and is related to U.S. Appl. No. 15/232,338.

An Office Action issued by the China National Intellectual Property Administration dated Apr. 25, 2019, which corresponds to Chinese Patent Application No. 201610653829.0 and is related to U.S. Appl. No. 15/232,338.

An Office Action mailed by the State Intellectual Property Office of the People's Republic of China dated Dec. 16, 2019, which corresponds to Chinese Patent Application No. 201610653829.0 and is related to U.S. Appl. No. 15/232,338.

* cited by examiner

FIG.8

GLUCOSE CONCENTRATION
134mg / dL

15 SEC CURRENT VALUE
/ 1.2 SEC CURRENT VALUE

| Hct (%) | 20 | 42 | 70 |
|---|---|---|---|
| n=1 | 0.93 | 1.21 | 1.37 |
| n=2 | 0.91 | 0.98 | 1.17 |
| n=3 | 1.03 | 1.21 | 1.31 |
| n=4 | 0.98 | 1.17 | 1.33 |
| n=5 | 1.02 | 1.20 | 1.34 |
| AVERAGE | 0.98 | 1.15 | 1.30 |

FIG.9

GLUCOSE CONCENTRATION
335mg / dL

15 SEC CURRENT VALUE
/ 1.2 SEC CURRENT VALUE

| Hct (%) | 20 | 42 | 70 |
|---|---|---|---|
| n=1 | 1.04 | 1.19 | 1.51 |
| n=2 | 1.05 | 1.16 | 1.49 |
| n=3 | 0.95 | 1.20 | 1.55 |
| n=4 | 1.04 | 1.05 | 1.47 |
| n=5 | 0.98 | 1.00 | 1.47 |
| AVERAGE | 1.01 | 1.12 | 1.50 |

MEASURING METHOD OF SENSOR USING INTERDIGITATED ARRAY ELECTRODE, MEASURING APPARATUS AND COMPUTER READABLE MEDIUM STORING MEASURING PROGRAM

CROSS-REFERENCE TO RELATED APPLICATION

The present application claims priority to Japanese Patent Application No. 2015-158357, filed Aug. 10, 2015, and Japanese Patent Application No. 2016-151022, filed Aug. 1, 2016, the entire contents of which are incorporated herein by reference.

FIELD

The embodiment pertains to a measuring method of a sensor using an interdigitated array electrode, a measuring apparatus and a measuring program.

BACKGROUND

A concentration of a target ingredient in a sample is measured by using a biosensor. For example, a measurement value of a target ingredient in a blood is influenced by a hematocrit value (Hct value) as the case may be. It is therefore fundamental to eliminate the influence of the Hct value in order to obtain a correct measurement value. The Hct value is a numerical value indicating a volume percentage of blood cells occupying a blood volume. Patent document 1 discloses, byway of specific Example, a method of manufacturing an interdigitated array electrode having a total planar dimension of electrodes, an inter-electrode distance and widths of the electrodes or the number of electrodes in a biosensor including the electrodes. Additionally, it is also disclosed that the Hct influence was lessened when measuring a glucose concentration in horse preserved blood by using the biosensor manufactured by this manufacturing method.

A system (e.g., Patent document 2) exists, which corrects a measurement value of glucose and other equivalent ingredients by providing an Hct electrode pair to measure the Hct value in addition to an electrode pair for measuring the glucose in order to reduce influence of the Hct value. There also exists a measuring method (e.g., Patent document 3) of correcting the influence of the Hct value on the measurement of the objective ingredient by acquiring a plurality of signals derived from an objective ingredient in the sample containing red blood cells by use of the biosensor and referring to a relation between a quantity of the objective ingredient and the plurality of signals corresponding thereto.

[Patent document 1] International Publication Pamphlet No. WO 2014/112569
[Patent document 2] U.S. Patent Application Publication No. 2011/0139634
[Patent document 3] Japanese Laid-open Patent Publication No. 2011-075362

SUMMARY

Conventional technologies, though attempting to reduce the influence of the Hct value, are requested to measure a concentration of a target ingredient with higher accuracy. In the case of separately providing the Hct electrode pair in addition to the electrode pair for measuring the glucose, this configuration causes a complicated structure of the sensor and intricacy of a connector, of a meter, corresponding to the electrodes of the sensor. It is an object of the embodiment, which was devised in view of the circumstances described above, to provide a technology of reducing the influence of the Hct value on the measurement of the target ingredient in the sample without separately providing the Hct electrode pair.

According to one aspect of the embodiment, the following configuration is adopted for accomplishing the object described above.

To be specific, one aspect of the embodiment pertains to a measuring method of measuring a concentration of a target ingredient in a sample by using a sensor including an interdigitated array electrode that includes a first electrode having a first comb tooth and a second electrode having a second comb tooth, and a reagent layer on the interdigitated array electrode, in which the first comb tooth and the second comb tooth are alternately arrayed, the measuring method including:

applying a voltage to between the first electrode and the second electrode;

measuring a first current value of an electric current flowing between the first electrode and the second electrode;

measuring a second current value of the current flowing between the first electrode and the second electrode;

calculating the concentration of the target ingredient in the sample, based on a third current value;

calculating a correction value, based on the first current value and the second current value; and correcting the concentration of the target ingredient in the sample, based on the correction value.

In the measuring method according to one aspect of the embodiment, the third current value is the first current value or the second current value. In the measuring method according to one aspect of the embodiment, the first current value is measured in advance of the second current value. Further, in the measuring method according to one aspect of the embodiment, the measuring the first current value is executed after a transient current flows between the first electrode and the second electrode.

In the measuring method according to one aspect of the embodiment, the first current value is smaller than the second current value. Still further, in the measuring method according to one aspect of the embodiment, the correction value is a ratio of the second current value to the first current value. Yet further, in the measuring method according to one aspect of the embodiment, the sample is a blood sample and is subjected to a hematocrit correction based on the correction value.

One of the embodiment pertains to a measuring apparatus to measure a concentration of a target ingredient in a sample, the measuring apparatus including:

a sensor including an interdigitated array electrode that includes a first electrode having a first comb tooth and a second electrode having a second comb tooth, and a reagent layer on the interdigitated array electrode, in which the first comb tooth and the second comb tooth are alternately arrayed;

a measuring unit to apply a voltage to between the first electrode and the second electrode and to measure a first current value and a second current value of an electric current flowing between the first electrode and the second electrode; and a control unit configured to calculate the concentration of the target ingredient in the sample based on a third current value, to calculate a correction value based on the first current value and the second current value, and to correct the concentration of the target ingredient in the sample based on the correction value.

Further, one aspect of the embodiment may also be a program for making the computer, other devices, machines, etc realize any one of the functions described above. Still further, one aspect of the embodiment may also be a recording medium recorded with such a program, which can be read by the computer etc.

According to one aspect of the embodiment, it is feasible to reduce the influence of the Hct value on the measurement of the target ingredient in the sample without separately providing the Hct electrode pair.

BRIEF DESCRIPTION OF THE DRAWINGS

FIG. 8 is a table indicating a ratio (current value after 15 sec/current value after 1.2 sec).

FIG. 9 is a table indicating the ratio (current value after 15 sec/current value after 1.2 sec).

DESCRIPTION OF EMBODIMENTS

An embodiment of the present invention will hereinafter be described with reference to the drawings. The embodiment given below is an exemplification, and the present invention is not limited to a configuration of the following embodiment.

Figure 1:
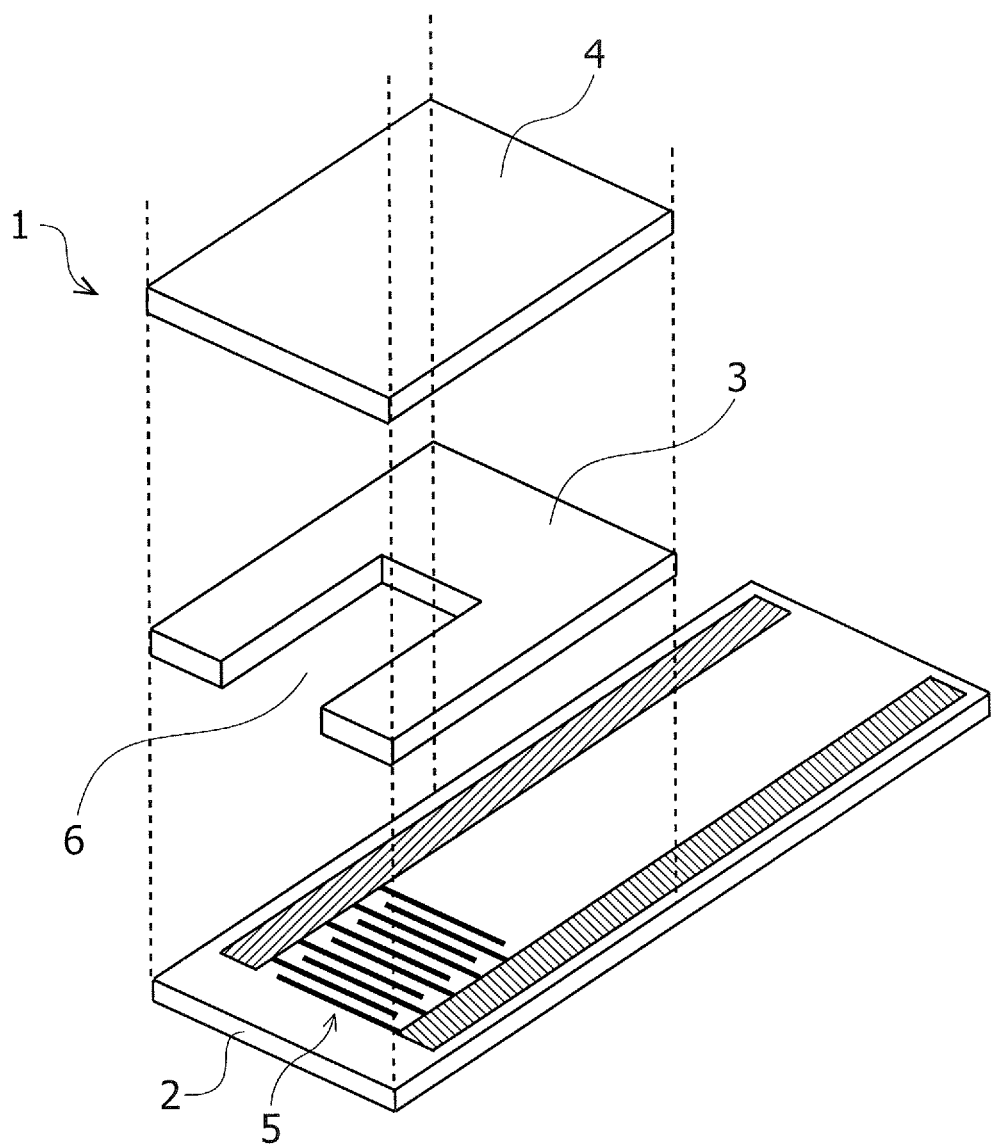
FIG. 1 is an exploded perspective view illustrating one example of a biosensor according to an embodiment.

FIG. 1 is an exploded perspective view illustrating one example of a biosensor 1 according to the embodiment. As illustrated in FIG. 1, the biosensor 1 includes a substrate 2, a spacer 3, a cover 4 and an interdigitated array electrode 5. The substrate 2, the spacer 3 and the cover 4 are composed of insulating materials instanced by a thermoplastic resin, a polyimide resin, an epoxy resin, glass, ceramics, paper and other equivalent materials. The thermoplastic resin includes polyether-imide (PEI), polyethylene terephthalate (PET), polyethylene (PE) and other equivalent resins.

The interdigitated array electrode 5 is formed by using a metal conductive material instanced by gold (Au), silver (Ag), platinum (Pt), palladium (Pd) and other equivalent metals. Any known materials may be applied to the substrate 2, the spacer 3, the cover 4 and the interdigitated array electrode 5. Sizes, i.e., dimensions and thicknesses of the substrate 2, the spacer 3, the cover 4 and the interdigitated array electrode 5 may be properly set.

The interdigitated array electrode 5 is formed on an upper surface of the substrate 2. An unillustrated reagent layer is formed on part of the interdigitated array electrode 5, and the spacer 3 is provided to cover part of the substrate 2 and the part of the interdigitated array electrode 5. The cover 4 is provided on the spacer 3. The spacer 3 is provided with a notch through which to expose the part of the interdigitated array electrode 5 and the reagent layer, and the cover 4 also covers an upper portion of the notch of the spacer 3, thus forming a capillary 6 inside the biosensor 1. A specimen is introduced into the capillary 6 by a capillary phenomenon, and a concentration of the specimen is thus measured.

The reagent layer contains, e.g., oxidation-reduction enzyme and a mediator (electron transfer substance). The oxidation-reduction enzyme and the mediator are properly selected corresponding to a type of target ingredient (specified substance) of a sample (specimen) to be measured. The sample to be measured is an erythrocyte containing sample instanced by a blood sample and other equivalent samples. The target ingredient in the sample is exemplified by glucose, lactate acid, urate acid, a ketone body and other equivalent ingredients.

The oxidation-reduction enzyme is exemplified by glucose oxidase (GOD), glucose dehydrogenase (GDH), lactate oxidase (LOD), urate oxidase (uricase) and other equivalent enzymes. A method of immobilizing the oxidation-reduction enzyme may involve adopting a variety of known methods, e.g., a method of utilizing an MPC (2-methacryloyloxyethyl phosphorylcholine) polymer produced by introducing a silane coupling agent into polymerized gel, macromolecules of polyacrylamide and phosphorus, and a phospholipid polymer, or utilizing a protein membrane.

The mediator may be exemplified by potassium ferricyanide, p-benzoquinone, phenazine methosulfate, indophenol, derivatives thereof, β-naphthoquinone-4-sulfonic acid potassium, methylene blue, ferrocene, derivatives thereof, osmium complex, ruthenium complex, NAD+ (nicotinamide adenine dinucleotide +), NADP+ (nicotinamide adenine dinucleotide phosphate +) and pyrroloquinoline quinone (PQQ).

Figure 2:
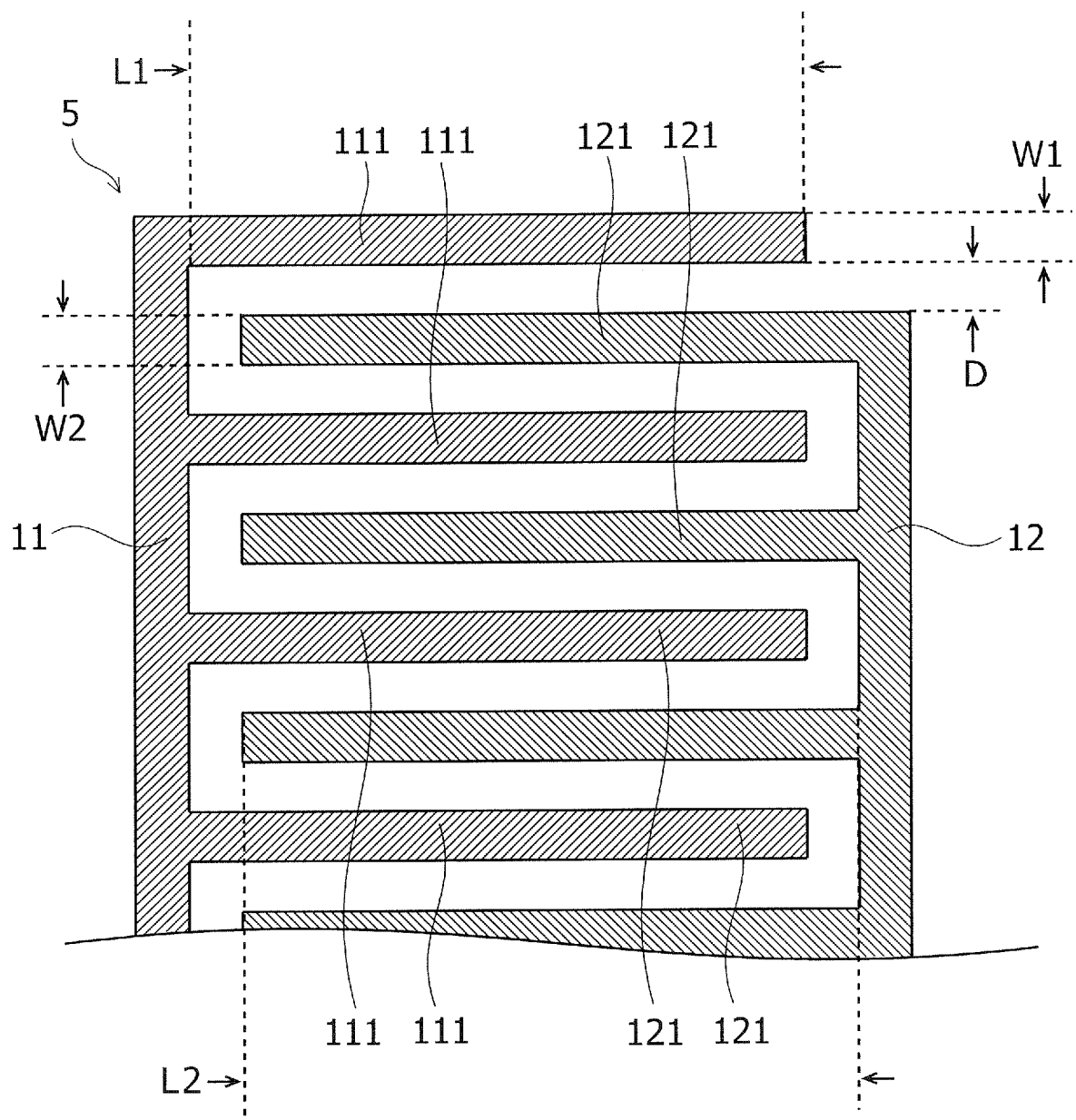
FIG. 2 is a plan view of an interdigitated array electrode.

FIG. 2 is a plan view of the interdigitated array electrode 5. As illustrated in FIG. 2, the interdigitated array electrode 5 includes a working electrode 11 and a counter electrode 12. The working electrode 11 is one example of a first electrode, while the counter electrode 12 is one example of a second electrode. Each of the working electrode 11 and the counter electrode 12 is formed in an interdigital shape. To be specific, the working electrode 11 has a plurality of comb teeth 111, and the counter electrode 12 has a plurality of comb teeth 121. The interdigitated array electrode 5 is configured so that the plurality of comb teeth 111 and the plurality of comb teeth 121 are arrayed to be alternately opposite to each other. The reagent layer is immobilized to the working electrode 11.

The working electrode 11 has an arbitrary number of comb teeth 111, and the counter electrode 12 also has an arbitrary number of comb teeth 121. It may be sufficient that the working electrode 11 has at least two comb teeth 111, and the counter electrode 12 has at least one comb tooth 121; or alternatively the working electrode 11 has at least one comb tooth 111, and the counter electrode 12 has at least two comb teeth 121. Preferably, e.g., the working electrode 11 may have 10 through 50 comb teeth 111, and the counter electrode 12 may also have 10 through 50 comb teeth 121. The comb tooth 111 of the working electrode 11 has a width (W1) taking an arbitrary value. For example, the width (W1) of the comb tooth 111 of the working electrode 11 may be set to preferably 5 μm through 50 μm and more preferably to 5 μm through 30 μm. The comb tooth 111 of the working electrode 11 has a length (L1) taking an arbitrary value. For example, the length (L1) of the comb tooth 111 of the working electrode 11 may be set to 0.1 mm through 2.0 mm.

The comb tooth 121 of the counter electrode 12 has a width (W2) taking an arbitrary value. For instance, the width (W2) of the comb tooth 121 of the counter electrode 12 may be set to 10 µm through 30 µm. The comb tooth 121 of the counter electrode 12 has a length (L2) taking an arbitrary value. For example, the length (L2) of the comb tooth 121 of the counter electrode 12 may be set to 0.1 mm through 2.0 mm. A distance (D) between the comb tooth 111 of the working electrode 11 and the comb tooth 121 of the counter electrode 12 takes an arbitrary value. For instance, the distance (D) between the comb tooth 111 of the working electrode 11 and the comb tooth 121 of the counter electrode 12 may be set to preferably 5 µm through 50 µm, and more preferably 5 µm through 30 µm.

Figure 3:
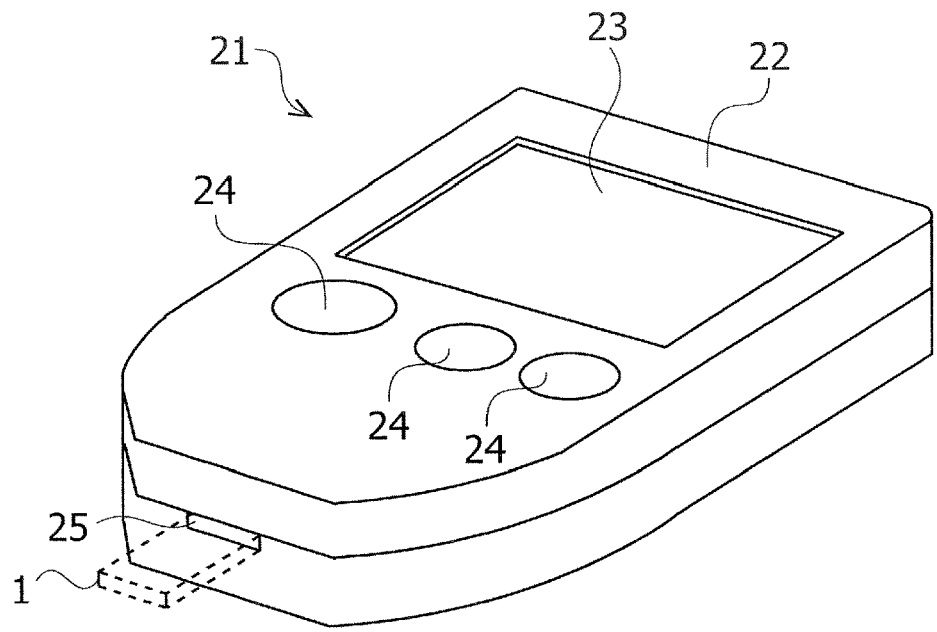
FIG. 3 is a perspective view illustrating one example of a measuring apparatus according to the embodiment.
Figure 4:
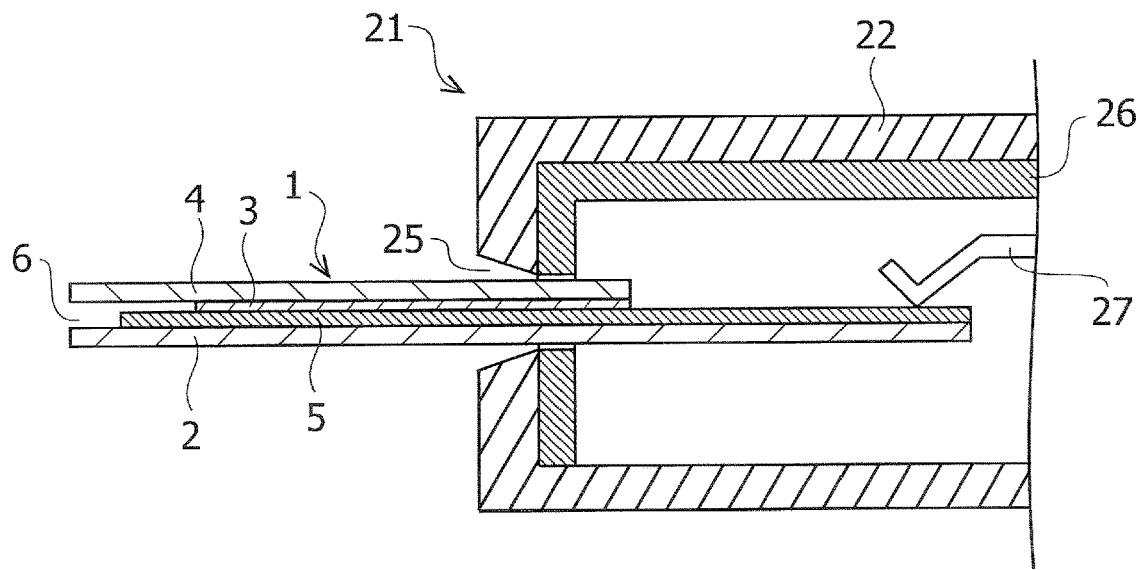
FIG. 4 is a partial sectional view of the measuring apparatus according to the embodiment.

FIG. 3 is a perspective view illustrating one example of a measuring apparatus 21 according to the embodiment. FIG. 4 is a partial sectional view illustrating the measuring apparatus 21 according to the embodiment. The measuring apparatus 21 measures the sample by an electrochemical method using the biosensor 1. The measuring apparatus 21 includes a housing 22, a display panel 23, operation buttons 24, a sensor insertion port 25, a fitting portion 26 and a connector 27. The measuring apparatus 21 has, though an illustration is omitted, a circuit board mounted with electronic components instanced by a CPU (Central Processing Unit), a RAM (Random Access Memory) and a ROM (Read Only Memory), which are fundamental for the measuring apparatus 21 to perform predetermined operations (such as applying a voltage and performing communications with the outside).

As illustrated in FIG. 4, the housing 22 is provided with the display panel 23 and the plurality of operation buttons 24. The display panel 23 displays a measurement result and an error, and also displays an operation procedure, an operation status and other equivalent operation items when setting. The display panel 23 is a display device instanced by a liquid crystal panel, a plasma display panel and an electroluminescence panel. The plurality of operation buttons 24 is used for a variety of settings (such as setting measurement conditions and inputting an examinee ID), and for operations such as starting and finishing the measurement. The plurality of operation buttons 24 may involve using a contact-type touch panel. The display panel 23 may be integrated with the operation buttons 24.

As depicted in FIG. 4, the biosensor 1 is inserted into the sensor insertion port 25 and is fitted to the fitting portion 26, in which case the interdigitated array electrode 5 of the biosensor 1 is electrically connected to the connector 27. When the specimen is introduced into the capillary 6, the voltage is applied to the interdigitated array electrode 5. Upon the voltage being applied to between the working electrode 11 and the counter electrode 12, the target ingredient in the sample is reduced by the oxidation-reduction enzyme. In other words, electrons are extracted from the target ingredient in the sample introduced into the capillary 6. The extracted electrons are supplied to the working electrode 11 via the mediator. An electric charge quantity of the electrons supplied to the working electrode 11 is measured as a response current.

Figure 5:
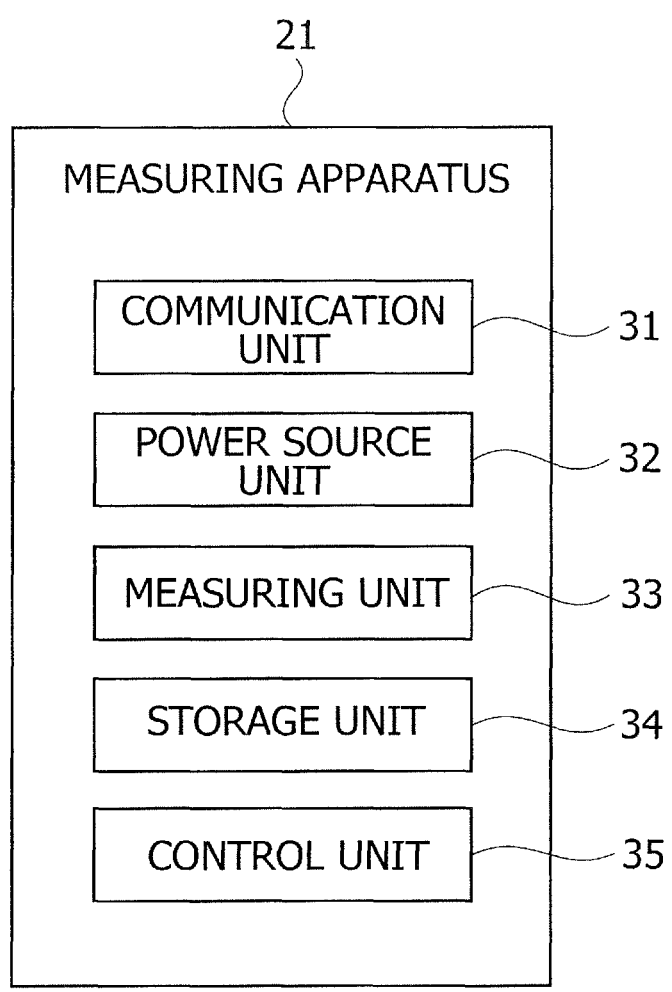
FIG. 5 is a diagram of a functional configuration of the measuring apparatus according to the embodiment.

Respective functions equipped in the measuring apparatus 21 will be described. FIG. 5 is a diagram of a functional configuration of the measuring apparatus 21 according to the embodiment. The measuring apparatus 21 includes a communication unit 31, a power source unit 32, a measuring unit 33, a storage unit 34 and a control unit 35.

The communication unit 31 performs data communications with other external devices. For example, The data communications may utilize, e.g., a wireless communication means (IrDA (Infrared Data Association) using infrared rays, or Bluetooth using a frequency band of 2.4 GHz). Wired data communications may also be performed by connecting the measuring apparatus 21 to other external devices via a cable instanced by USB (Universal Serial Bus). The power source unit 32 supplies electric power for activating the measuring apparatus 21. The power source unit 32 may be a primary battery instanced by a button battery, and may also be a secondary repetitive chargeable/dischargeable battery.

For measuring the concentration of the target ingredient in the sample, the measuring unit 33 applies the voltage to between the working electrode 11 and counter electrode 12 of the interdigitated array electrode 5 provided in the biosensor 1, thereby measuring a value of the current flowing between the working electrode 11 and the counter electrode 12. The measuring unit 33 controls, e.g., a voltage application timing, a value of the applied voltage and other equivalent items.

The measuring unit 33 measure the current at least twice during a period till a measurement result is displayed on the display panel 23 since completing preparations for measuring the concentration of the target ingredient in the sample ingredients. The current to be measured first time is referred to as a first current value, and the current to be measured second time is referred to as a second current value. A period of time till the first current value is measured since applying the voltage is termed first measurement time, and a period of time till the second current value is measured since applying the voltage is termed second measurement time. In-depth descriptions of the first and second current values and the first and second measurement time, will be made later on.

The storage unit 34 stores programs, various items of data and other equivalent software, which are fundamental to a variety of arithmetic operations. The storage unit 34 is previously stored with calibration curve data representing a corresponding relation between the current values and the concentrations of the target ingredients in the samples, in which the current values are acquired by using the known samples with the concentrations being known of the target ingredients in the samples. The calibration curve data are stored as, e.g., mathematical expressions and a corresponding table in the storage unit 34.

The control unit 35 refers to a calibration curve based on the measured current values, thus calculating (measuring) the concentration of the target ingredient in the sample. The current value used for calculating the concentration of the target ingredient in the sample may be the first current value, may also be the second current value, and may further be a current value (third current value) at a spot other than those of the first and second current values. The third current value may be measured before, e.g., the first measurement time, may also be measured between the first measurement time and the second measurement time, and may further be measured after the second measurement time. The control unit 35 may calculate the concentration of the target ingredient in the sample on the basis of the first current value or the second current value. The third current value is set as the first current value or the second current value, in which case this setting has an advantage of decreasing a current measurement count.

The control unit 35 calculates a correction value (correction coefficient), based on the first current value and the second current value. The correction value is a ratio of the second current value to the first current value (second current value/first current value), and is also data for correcting the concentration of the target ingredient in the sample. The control unit 35 calculates the correction value by dividing the second current value by the first current value. The control unit 35 corrects, based on the correction value, the concentration of the target ingredient in the sample.

Figure 6:
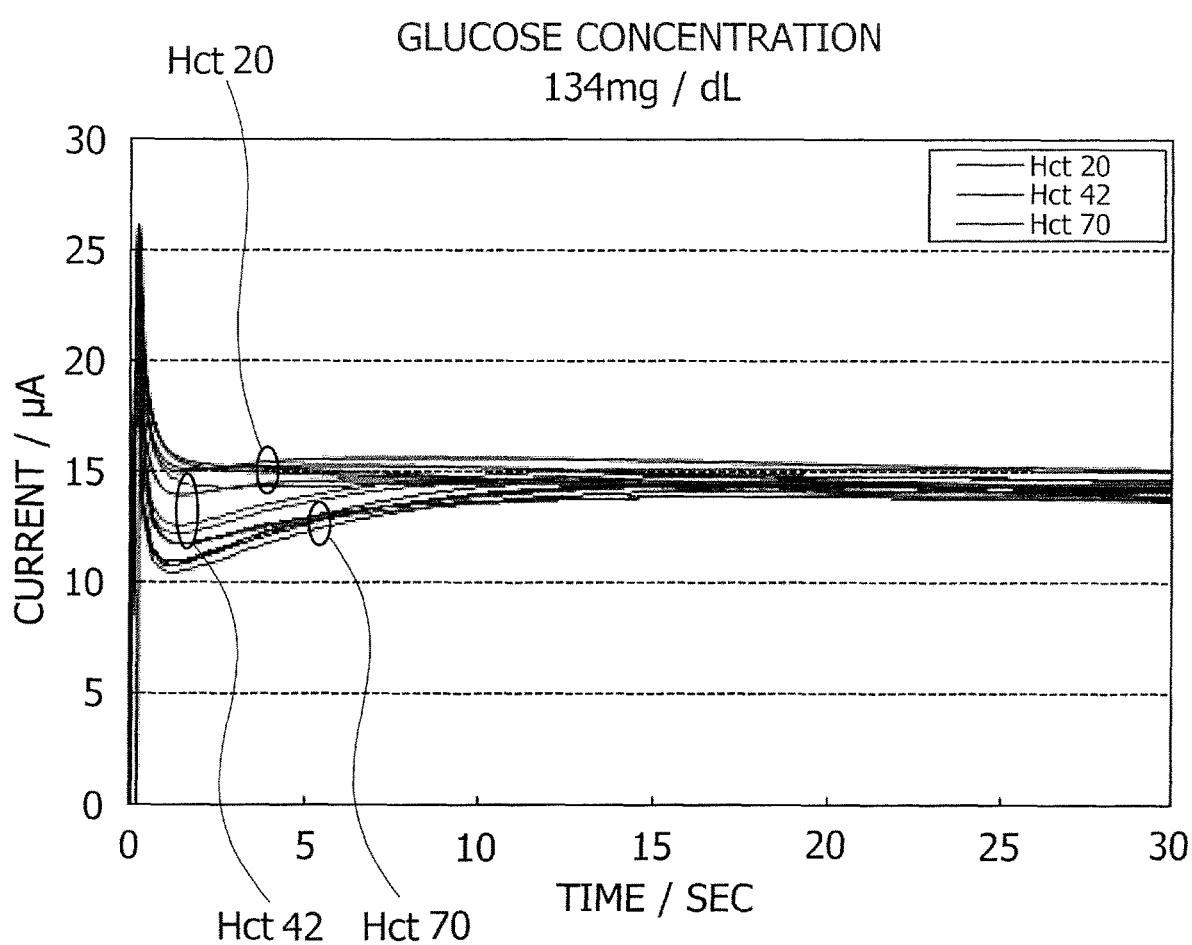
FIG. 6 is a graph depicting a change with the passage of time in current value.
Figure 7:
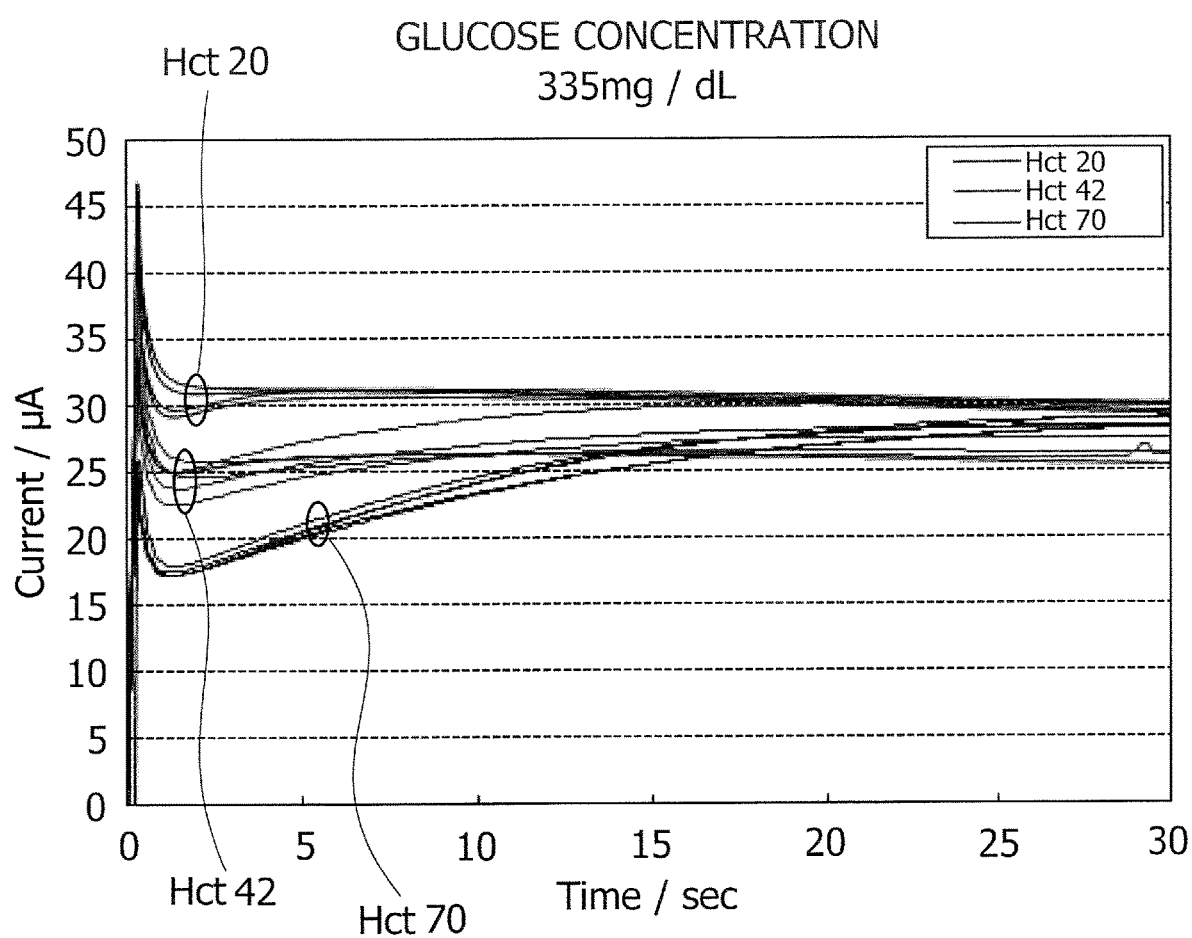
FIG. 7 is a graph depicting the change with the passage of time in current value.

Herein, a relation between the ratio of the second current value to the first current value and an Hct (hematocrit) value will be described. FIGS. 6 and 7 are graphs each depicting a change with the passage of time in current value (time course) in the measurement by a chronoamperometry method of applying a voltage of +200 mV at a temperature of 25° C. (±1° C.). Prepared are the specimens having glucose concentrations of 134 mg/dL and 335 mg/dL, and three types of samples having Hct values that are 20%, 42% and 72% are created for the respective specimens. FIG. 6 illustrates the change with the passage of time in current value with respect to the glucose concentration of 134 mg/dL, and FIG. 7 illustrates the change with the passage of time in current value with respect to the glucose concentration of 335 mg/dL.

The current measurements in FIGS. 6 and 7 are made by using an electrochemical analyzer of a 2-electrode system. The working electrode (WE) and the counter electrode (CE) involve using the gold (Au)-based interdigitated array electrode 5.

The following are the sizes of the working electrode and the counter electrode each used for the current measurements in FIGS. 6 and 7.

Width (W1) of Comb Tooth 111 of Working Electrode 11/Width (W2) of Comb Tooth 121 of Counter Electrode 12/Inter-Comb-Teeth Distance (D) (Distance between Comb Tooth 111 and Comb Tooth 121)=30 μm/30 μm/30 μm Length (L1) of Comb Tooth 111 of Working Electrode 11/Length (L2) of Comb Tooth 121 of Counter Electrode 12=1.4 mm/1.4 mm The number of the comb teeth 111 of the working electrode 11 is "13", and the number of the comb teeth 121 of the counter electrode 12 is "13".

A planar dimension (as viewed on the plane) of the working electrode 11 is 0.546 mm$^2$, and a planar dimension (as viewed on the plane) of the counter electrode 12 is 0.546 mm$^2$.

A capacity of the capillary 6 of the biosensor 1 used for the current measurements in FIGS. 6 and 7 is 0.8 μL.

The biosensor, of which the reagent layer was formed by applying a reagent solution adjusted as below onto the interdigitated array electrode 5, was used for the current measurements in FIGS. 6 and 7.
Mediator (1M potassium ferricyanide): 150 mM
Protective agent (30% sucrose): 0.5%
Phosphate buffer (pH7.0): 100 mM
Enzyme: 3 U/chip
1.2% synthetic smectite: 0.3%

FIGS. 6 and 7 depict the current values when the Hct values are 20%, 42% and 70%. Application of the voltage to the interdigitated array electrode 5 was started after 1 sec subsequent to introducing the sample by connecting the biosensor 1 to the connector 27. As illustrated in FIGS. 6 and 7 with the measurements being made after 15 sec subsequent to applying the voltage, transient responses exhibiting acute peaks occurred in the glucose concentrations immediately after the voltage application was started. In other words, transient currents flow immediately after the start of the voltage application. As illustrated in FIGS. 6 and 7, differences between the changes with the passage of time (time course) in current value are seen in terms of the Hct values.

When the Hct value is 20%, no large change is seen in current value after a decrease in current value subsequent to the transient response, the current indicates a substantially fixed value. When the Hct values are 42% and 70%, the current values decrease after the transient responses, then gently rise after exhibiting negative peaks, and thereafter remain stable as substantially fixed values. The change with the passage of time in current value indicates the same tendency with respect to the glucose concentration of 134 mg/dL and the glucose concentration of 335 mg/dL. A decline of current, which is caused after the transient response, is larger as the Hct value is higher. A tendency of the change with the passage of time in current value therefore depends on the Hct value irrespective of the glucose concentration. Hence, the correction coefficient is calculated by using the change with the passage of time in current value, thereby enabling the Hct value to be estimated and the glucose concentration to be corrected.

The first current value was measured after 1.2 sec subsequent to a start of applying the voltage, and the second current value was measured after 15 sec subsequent to the start of applying the voltage. In this case, the first measurement time is 1.2 sec, and the second measurement time is 15 sec. The glucose concentration was calculated based on the second current value measured after 15 sec subsequent to applying the voltage by using the calibration curve, an Hct correction described below was thereafter made, and a final glucose concentration was measured. FIGS. 8 and 9 are tables each indicating the ratios of the second current value to the first current value. In FIGS. 8 and 9, the current values are measured five times when the Hct values are 20%, 42% and 70%. The ratio of the second current value (measured after 15 sec) to the first current value (measured after 1.2 sec) will hereinafter be referred to as the ratio (current value after 15 sec/current value after 1.2 sec). As illustrated in FIGS. 8 and 9, the ratio (current value after 15 sec/current value after 1.2 sec) differs corresponding to a magnitude of the glucose concentration but rises as the Hct value increases. The first current value (measured after 1.2 sec) is, though some variations occur depending on the Hct value, totally smaller than the second current value (measured after 15 sec). Accordingly, the correction value is calculated based on the ratio between the current values at the two measuring points, and it is feasible to calculate the Hct value from the corresponding tables as depicted in FIGS. 8 and 9 on the basis of the calculated correction value. Note that the Hct correction was conducted by using the correction value in the discussion given above, and the glucose concentration may, however, be corrected by use of an Hct concentration by calculating this Hct concentration from the ratio (current value after 15 sec/current value after 1.2 sec).

The method of correcting the glucose concentration based on the Hct value may involve adopting a variety of methods, e.g., a method of using a correction table, the calibration curve data and other equivalent information. The discussion given above has described the case in which the target ingredient in the sample of the glucose, and the embodiment is not, however, limited to the glucose as the target ingredient in the sample. For example, when the target ingredients in the sample are the lactate acid, the urate acid, the ketone body and other equivalent ingredients, the correction value is calculated based on the ratio between the current values at the two points of time, and it is possible to calculate the Hct value from the corresponding table on the basis of the calculated correction value. The method of correcting the concentrations of the lactate acid, the urate acid, the ketone body and other equivalent ingredients on the basis of the Hct value may involve adopting a variety of known methods, e.g., a method using a correction table, calibration curve data and other equivalent information.

In the embodiment described above, the application of the voltage was started after 1 sec subsequent to introducing the sample; the first current value was measured after 1.2 sec subsequent to applying the voltage; the second current value was measured after 15 sec subsequent to applying the voltage; and the measurement time may, however, be properly determined corresponding to a period of time expended till applying the voltage since after introducing the specimen, and the measurement conditions. For instance, after applying the voltage to the interdigitated array electrode 5, any one of values, i.e., 0.1 sec, 0.2 sec, 0.3 sec, 0.4 sec, 0.5 sec, 0.6 sec, 0.7 sec, 0.8 sec, 0.9 sec, 1.0 sec, 1.1 sec, 1.2 sec, 1.3 sec, 1.4 sec, 1.5 sec, 1.6 sec, 1.7 sec, 1.8 sec, 1.9 sec and 2.0 sec, may be set as the first measurement time. A value given by adding 0.1 sec to the first measurement time maybe set as the second measurement time. After applying the voltage to the interdigitated array electrode 5, any one of values, i.e., 1 sec, 2 sec, 3 sec, 4 sec, 5 sec, 10 sec, 15 sec, 20 sec, 30 sec, 40 sec, 50 sec, 1 min, 1 min 30 sec, 2 min, 2 min 30 sec, 3 min, 3 min 30 sec, 4 min, 4 min 30 sec and 5 min, may be set as the second measurement time.

Note that it is desirable for the first current value to be measured after the transient response in order to enhance measurement accuracy, and it is more preferable to measure the current value at a spot indicating the smallest current value after the transient current. The second current value maybe measured anytime as far as after the measurement of the first current value; and it is, however, suitable to measure a stable current value as the second current value occurring after a gentle rise of the current value because of a large difference between the first current value and the second current value being preferable for enhancing the measurement accuracy. The start time for applying the voltage may not be after 1 sec subsequent to introducing the sample, and the application of the voltage may be started immediately after introducing the sample and may also be started at an interval of 1 sec or longer subsequent to introducing the sample.

The storage unit 34 previously stores a corresponding table (which will hereinafter be termed an Hct corresponding table) containing the correction value acquired by using such a sample that the concentration of the target ingredient is already known and the Hct value by associating these values with each other. The control unit 35 calculates (extracts) the Hct value from the Hct corresponding table on the basis of the correction value. The control unit 35 corrects, based on the Hct value, the concentration of the target ingredient in the sample. The control unit 35 displays, on the display panel 23, the concentration (post-correcting concentration) of the target ingredient in the sample after being corrected.

The measuring unit 33 may measure, as the first current value, a value of the current flowing between the working electrode 11 and the counter electrode 12 a plural number of times during a period till first predetermined time elapses since after starting the application of the voltage. An arbitrary period of time may beset as the first predetermined time. The same value as the first measurement time may also be set as the first predetermined time. The measuring unit 33 may measure, as the second current value, a value of the current flowing between the working electrode 11 and the counter electrode 12 a plural number of times during a period till second predetermined time elapses since after an elapse of the first predetermined time. An arbitrary period of time may be set as the second predetermined time. The same value as the second measurement time may also be set as the second predetermined time. The control unit 35 may calculate a plurality of correction values on the basis of a plurality of first current values measured during the period till the elapse of the first predetermined time since after starting the application of the voltage and a plurality of second current values measured during the period till the elapse of the second predetermined time since after the elapse of the first predetermined time. The control unit 35 performs an arithmetic operation to average the plurality of correction values, and may correct the concentration of the target ingredient in the sample, based on the averaged correction value.

Figure 10:
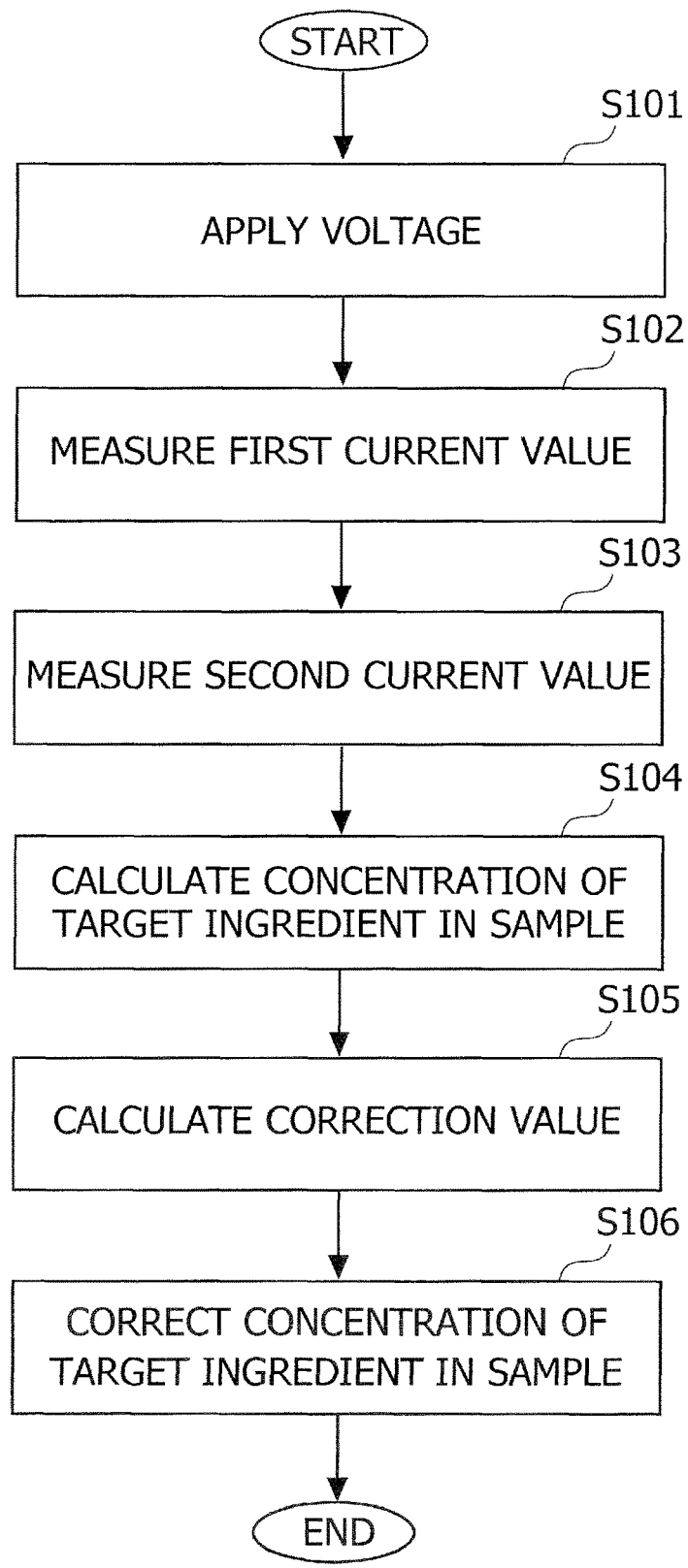
FIG. 10 is a flowchart illustrating one example of a process of measuring a concentration of a target ingredient in a sample by a measuring apparatus.

FIG. 10 is a flowchart illustrating one example of of a process of measuring the concentration of the target ingredient by the measuring apparatus 21. For example, a start of the flow illustrated in FIG. 10 is triggered by an event that the control unit 35 accepts a start process of measuring the concentration of the target ingredient, upon operating the operation button 24 of the measuring apparatus 21. To give another example, the start of the flow illustrated in FIG. 10 may be triggered by an event that the control unit 35 detects fitting of the biosensor 1, upon the biosensor 1 being fitted to the measuring apparatus 21.

In step S101, the measuring unit 33 applies the voltage to between the working electrode 11 and the counter electrode 12 of the interdigitated array electrode 5. The applied voltage is properly set corresponding to the type of the target ingredient in the sample. In step S102, the measuring unit 33 measures the first current value of the current flowing between the working electrode 11 and the counter electrode 12. The measuring unit 33 stores the first current value in the storage unit 34. In step S103, the measuring unit 33 measures the second current value of the current flowing between the working electrode 11 and the counter electrode 12. The measuring unit 33 stores the second current value in the storage unit 34.

In step S104, the control unit 35 calculates the concentration of the target ingredient in the sample on the basis of the first current value or the second current value. In step S105, the control unit 35 calculates the correction value on the basis of the first current value and the second current value. In step S106, the control unit 35 corrects the concentration of the target ingredient in the sample. The control unit 35 stores the post-correcting concentration of the target ingredient in the sample in the storage unit 34. The control unit 35 displays a measurement result (the post-correcting concentration of the target ingredient in the sample) on the display panel 23. When an error occurs in the measurement, the control unit 35 displays the error (error message) on the display panel 23. The control unit 35 may display the measurement result on the display panel 23, corresponding to the operation on the operation button.

According to the embodiment, it is not fundamental to separately provide the biosensor 1 with an electrode pair for measuring the Hct value. It is therefore feasible to reduce influence of the Hct value on the target ingredient in the sample by at least two electrodes. The biosensor 1 is not separately provided with the electrode pair for measuring the Hct value, and hence a connector count of the measuring apparatus 21 is restrained from increasing. It is therefore possible to reduce the influence of the Hct value on the target ingredient in the sample without increasing the connector count of the measuring apparatus 21, thus leading to a decrease in costs of the measuring apparatus 21. The connector count of the measuring apparatus 21 does not increase, and it is therefore feasible to reduce the influence of the Hct value on the target ingredient in the sample with the simple configuration of the apparatus. According to the embodiment, it is possible to satisfy a standard (±10% of the Hct value of 42%) of ISO15197:2013 within an Hct value range of 20% through 70%.

<<Description Relating to Computer-Readable Medium>>

Any of the functions of the embodiment described above may be encoded and stored in a storage area of a computer-readable medium. In this case, a program for realizing the function may be provided to the computer, or to a computer incorporated into a machine or an apparatus, via the computer-readable medium. The function can be realized by having the computer, or the computer incorporated into a machine or an apparatus, read the program from the storage area of the computer-readable medium and execute the program.

Here, the computer-readable medium denotes a recording medium that employs an electric, magnetic, optical, chemical, physical, or mechanical action to accumulate information such as programs and data and holds the information in a condition that allows reading thereof to a computer. A flexible disk, a magneto-optical disk, a CD-ROM, a CD-R/W, a DVD, a DAT, 8 mm tape, a memory card, and so on may be cited as examples of recording media that can be attached to and detached from a computer. Further, a hard disk, a ROM, and so on may be cited as recording media that are fixed to a computer.

What is claimed is:

1. A measuring method of measuring a corrected concentration value of a target ingredient in a sample by using a sensor including an interdigitated array electrode that includes a first electrode having a first comb tooth and a second electrode having a second comb tooth, and a reagent layer on the interdigitated array electrode, in which the first comb tooth and the second comb tooth are alternately arrayed, the measuring method comprising:
    applying a constant voltage to between the first electrode and the second electrode;
    measuring a first current value of an electric current flowing between the first electrode and the second electrode in applying the constant voltage;
    measuring a second current value of the current flowing between the first electrode and the second electrode in applying the constant voltage;
    wherein the constant voltage is continuously applied during the step of measuring the first current value and the step of measuring the second current value;
    calculating a concentration value of the target ingredient in the sample, based on a third current value to obtain a calculated concentration value;
    calculating a correction value which is a ratio of the second current balue to the first current value; and
    correcting the calculated concentration value of the target ingredient in the sample with a comparison between the calculated concentration value of the target ingredient with the correction value, and adjusting the calculated concentration value of the target ingredient based on the comparison to obtain the corrected concentration value.

2. The measuring method according to claim 1, wherein the third current value is the first current value or the second current value.

3. The measuring method according to claim 1, wherein the first current value is measured in advance of the second current value.

4. The measuring method according to claim 3, wherein the measuring the first current value is executed after a transient current flows between the first electrode and the second electrode.

5. The measuring method according to claim 1, wherein the first current value is smaller than the second current value.

6. The measuring method according to claim 1, wherein the sample is a blood sample and is subjected to a hematocrit correction based on the correction value.

7. A non-transitory computer-readable medium storing a measuring program for measuring a corrected concentration of a target ingredient in a sample by using a sensor including an interdigitated array electrode that includes a first electrode having a first comb tooth and a second electrode having a second comb tooth, and a reagent layer on the interdigitated array electrode, in which the first comb tooth and the second comb tooth are alternately arrayed, the measuring program causing a computer to execute a procedure, the procedure comprising:
    applying a constant voltage to between the first electrode and the second electrode;
    measuring a first current value of an electric current flowing between the first electrode and the second electrode in applying the constant voltage;
    measuring a second current value of the current flowing between the first electrode and the second electrode in applying the constant voltage;
    wherein the constant voltage is continuously applied during the step of measuring the first current value andd the step of measuring the second current value;
    calculating a concentration value of the target ingredient in the sample, based on a third current value to obtain a calculated concentration value;
    calculating a correction value which is a ratio of the second current value to the first current value; and
    correcting the calculated concentration of the target ingredient in the sample with a comparison between the calculated concentration value of the target ingredient with the correction value, and adjusting the calculated concentration value of the target ingredient based on the comparison to obtain the corrected concentration value.

* * * * *